United States Patent [19]

Schick et al.

[11] 4,183,791
[45] Jan. 15, 1980

[54] METHOD OF FORMING AMPEROMETRIC SENSOR WITH TRANSITION METAL OXIDE/HYDROXIDE ELECTRODES

[76] Inventors: Karl G. Schick, 5050 N. 19th St., Milwaukee, Wis. 53209; Calvin O. Huber, 707 W. Pioneer Rd., Mequon, Wis. 53092

[21] Appl. No.: 898,516

[22] Filed: Apr. 20, 1978

[51] Int. Cl.² .............................................. C25D 9/06
[52] U.S. Cl. ................................................ 204/56 R
[58] Field of Search ............................... 204/56 R, 96

[56] References Cited

U.S. PATENT DOCUMENTS

| | | | |
|---|---|---|---|
| 3,335,033 | 8/1967 | Hober | 204/56 R |
| 3,389,061 | 6/1968 | Bono | 204/56 R |
| 3,498,893 | 3/1970 | Henderson et al. | 204/56 R |
| 3,579,383 | 5/1971 | Turner | 204/56 R |

*Primary Examiner*—R. L. Andrews
*Attorney, Agent, or Firm*—McDougall, Hersh & Scott

[57] ABSTRACT

An amperometric sensor device for electrochemical determination of polyhydroxy and polyamine compounds in liquid chromatography and high pressure liquid chromatography in which use is made of an electrode formed of a substrate of transition metals having a surface layer formed of a multivalent oxide/hydroxide of the metal and in which the anionic vacancies in the coating are partially filled with halide or sulfide ions and/or in which cationic vacancies are at least partially filled with alkali metal ions.

7 Claims, 3 Drawing Figures

METHOD OF FORMING AMPEROMETRIC SENSOR WITH TRANSITION METAL OXIDE/HYDROXIDE ELECTRODES

The invention relates to a new amperometric sensor device for the detection and determination of aliphatic and aromatic hydroxy compounds (mono- and polyhydroxy), of aliphatic and aromatic amides or amines (mono- and polyamines), of aliphatic and aromatic thiols (mono- and polythiols) and of hydrogen peroxide.

In our copending application Ser. No. 772,454, filed Feb. 28, 1977, and entitled "Amperometric Non-Enzymatic Method of Determining Sugars and Other Polyhydroxy Compounds," description is made of a method of determination of hydrogen peroxides, sugars and other polyhydroxy compounds by means of an electrochemical oxidation with a transition metal oxide catalyst. The method is based on a three-electrode system consisting of a saturated Calomel reference electrode, a platinum counter electrode, and a working electrode, the working electrode comprising a disc of platinum or gold electrochemically plated with a mixture of lead dioxide and nickel oxides.

M. Fleischmann, K. Korinek and D. Pletcher, J. C. S. Perkin II pages 1396–1403 (1972) describe the kinetics and mechanism of the oxidation of amines and alcohols at oxide covered nickel, silver, copper and cobalt electrodes but use in an amperometric sensor device is believed to represent a new and novel use.

It is an object of this invention to provide an improved sensor device which can be applied to the catalytic oxidation of polyamines and polyhydroxyl compounds in liquid chromatography (LC) and high pressure liquid chromatography systems (HPLC).

It is a further object of this invention to provide an improved amperometric sensor device which can be used for the determination of mono- and polyhydroxyl, mono- and polyamine, thiol and hydrogen peroxide compounds in LC and HPLC systems and it is a related object to provide a method for carrying out the same.

In accordance with the practice of this invention, use is made of an amperometric sensor having an electrode, the surface of which comprises multivalent transition metal oxides/hydroxides. Furthermore, surfaces consisting of conductive mixtures of transition metal oxides/hydroxides and/or transition metal halides capable of forming solid solutions can also be used. The same applies to conductive mixtures of transition metal oxides/hydroxides and/or transition metal sulfides.

"Transition elements include elements 21 through 29 (Sc through Cu), 39–47 (Y through Ag), 57–79 (La Through Au) and all known elements from 89 (Ac) on." The condensed Chemical Dictionary, 9th Ed. P. 873, Van Nostrand Reinhold Co. N.Y. 1977.

The formation of isostructurally related transition metal oxides/hydroxides and transition metal halides or transition metal sulfides allows the rapid interdiffusion of these compounds at the electrode surface. Such solid state mixtures are referred to as "solid solutions". However, if isostructures are not formed, nucleation and growth of different solid state phases occurs at the electrode surface which ultimately may deteriorate the electrode response.

The transition metal is selected from the metals of the periods 4, 5 and 6 of the periodic table which give, by anodic oxidation in a basic solution, a superior valence oxide with at least one active oxygen atom, and preferably, from the group comprising copper, cobalt, nickel and silver and mixtures thereof. These metals own an inferior valence oxide (or hydroxide) ($Cu_2O$, $CoO$, $NiO$ and $Ag_2O$) and give, by anodic oxidation in a basic solution, a superior valence oxide/hydroxide ($CuO$, $Co_2O_3$, $Ni_2O_3$, $AgO$) in which at least one species is active and may act as oxidizing agent.

The invention will hereinafter be illustrated by reference to the following drawings in which FIG. 1 is an elevational view of the separated elements of the sensor embodying the features of this invention, shown in their relative position for assembly;

Figure 1:
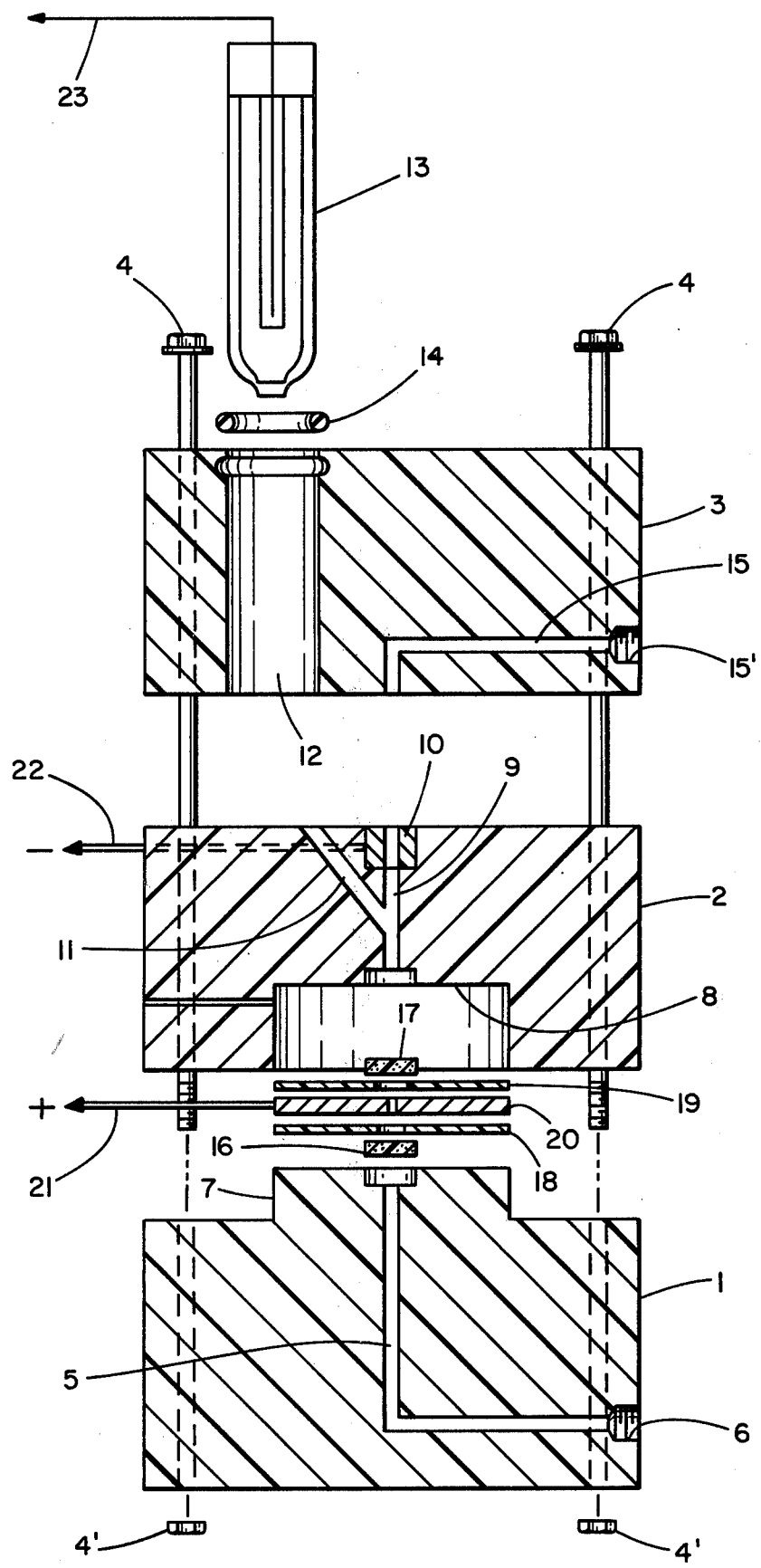

The following examples will illustrate the practice of the invention in the preparation of the amperometric sensor device and in the method for carrying out said amperometric sensors in the determination of mono- and polyhydroxy, mono- and polyamines, mono- and polythiols and hydrogen peroxide compounds in an LC system.

EXAMPLE 1

Preparation of Electrode

An electrode embodying the features of this invention is shown in the drawings as an assembly of three cylindrical blocks 1, 2 and 3 which may be formed of such resinous materials as an acrylic resin to a diameter, such as 1 3/16". The shape and dimensions of the blocks are not critical. The blocks are formed with aligned passages h-h for purposes of joinder into an assembled relation, as by means of bolts or rods 4, having a head at one end and a threaded portion at the other for threaded engagement by a fastening nut 4'.

The lower block 1 is formed with an axial passage 5 which communicates with a latter passage 5' which terminates with an adaptor 6 for connection with the source of solution to be analyzed. The top side of the block 1 is formed with a projection 7 which is adapted to be received in telescoping relation within a recessed portion 8 in the base of the middle block 2.

The middle block 2 is provided with an axial passage 9 which extends from the recess 8 through the upper portion of the block to a well 9' in which a platinum electrode 10 is received in fitting relation with the passage 9' continuing through the electrode. The passage 9 has a branck 11 which extends angularly upwardly into registry with a cavity 12 through the upper block 3, into which a standard saturated Calomel electrode 13 is inserted. A sealing relation between the upper end of the inserted Calomel electrode and the block is maintained by a sealing gasket, such as an O-ring 14.

The upper block 3 is provided with a channel 15 which communicates with the channel 9 of the middle block and extends laterally to a means 15' for connection for drainage of the solution after analysis.

The active elements of the amperometric sensor are inserted in the cavity 8 for location between the blocks 1 and 2. This comprises two porous teflon washers 16 and 17 which function as mechanical filters, a pair of washers 18 and 19, which may be formed of polyethylene, dimensioned to be received in aligned recesses 8' and 7', and a disc 20 formed of copper, nickel, cobalt or silver with a narrow axial passage therethrough. The disc is connected by an electrical conductor 21 to the test apparatus. The platinum electrode 10 and the Calomel electrode 13 are also provided with electrical conductors 22 and 23 respectively.

The three blocks 1, 2 and 3 and the parts 15-21 are clamped together in a sealed relation by means of the screw rods 4.

Figure 2:
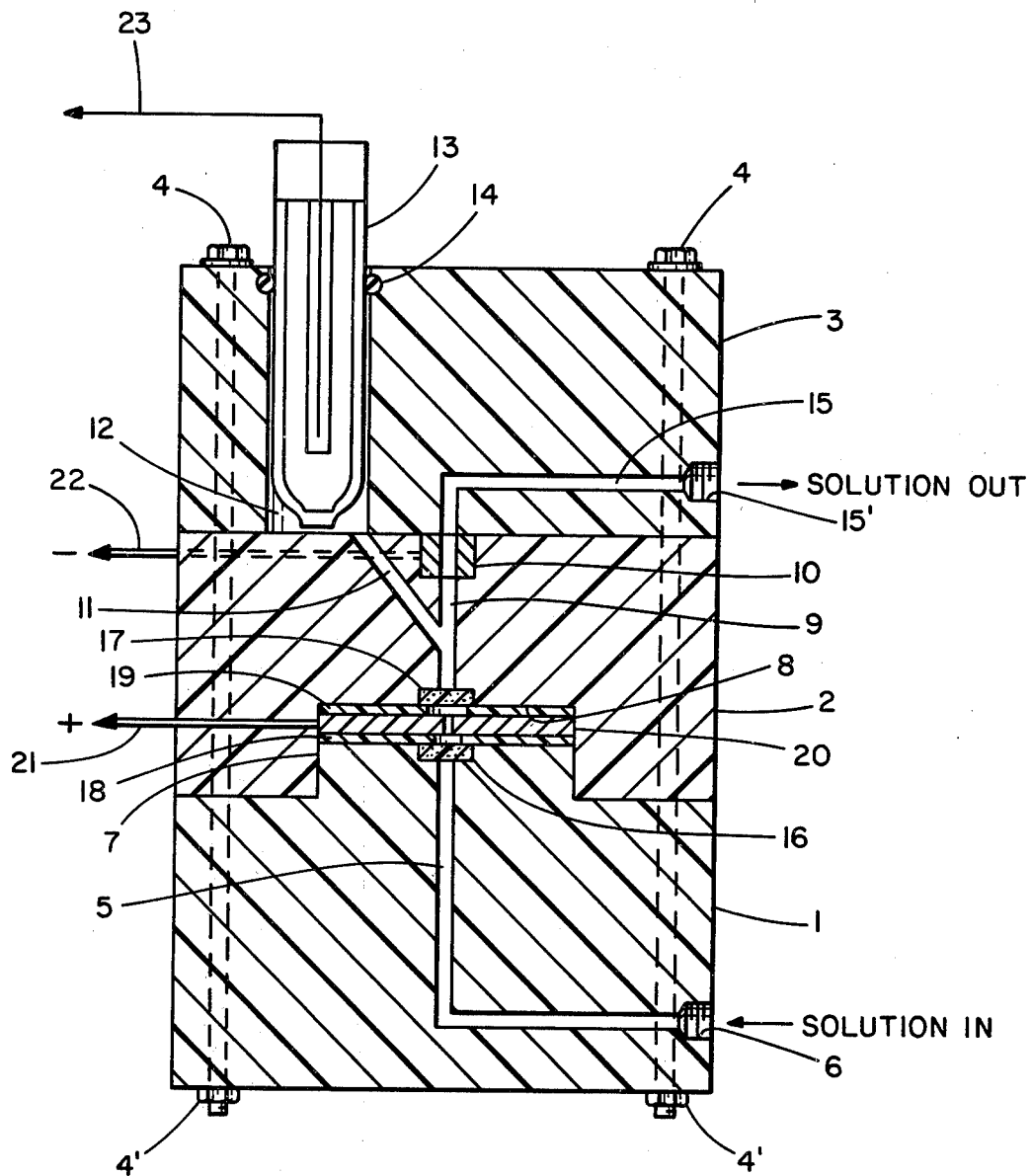
FIG. 2 is an elevational view of the assembled parts of FIG. 1.
Figure 3:
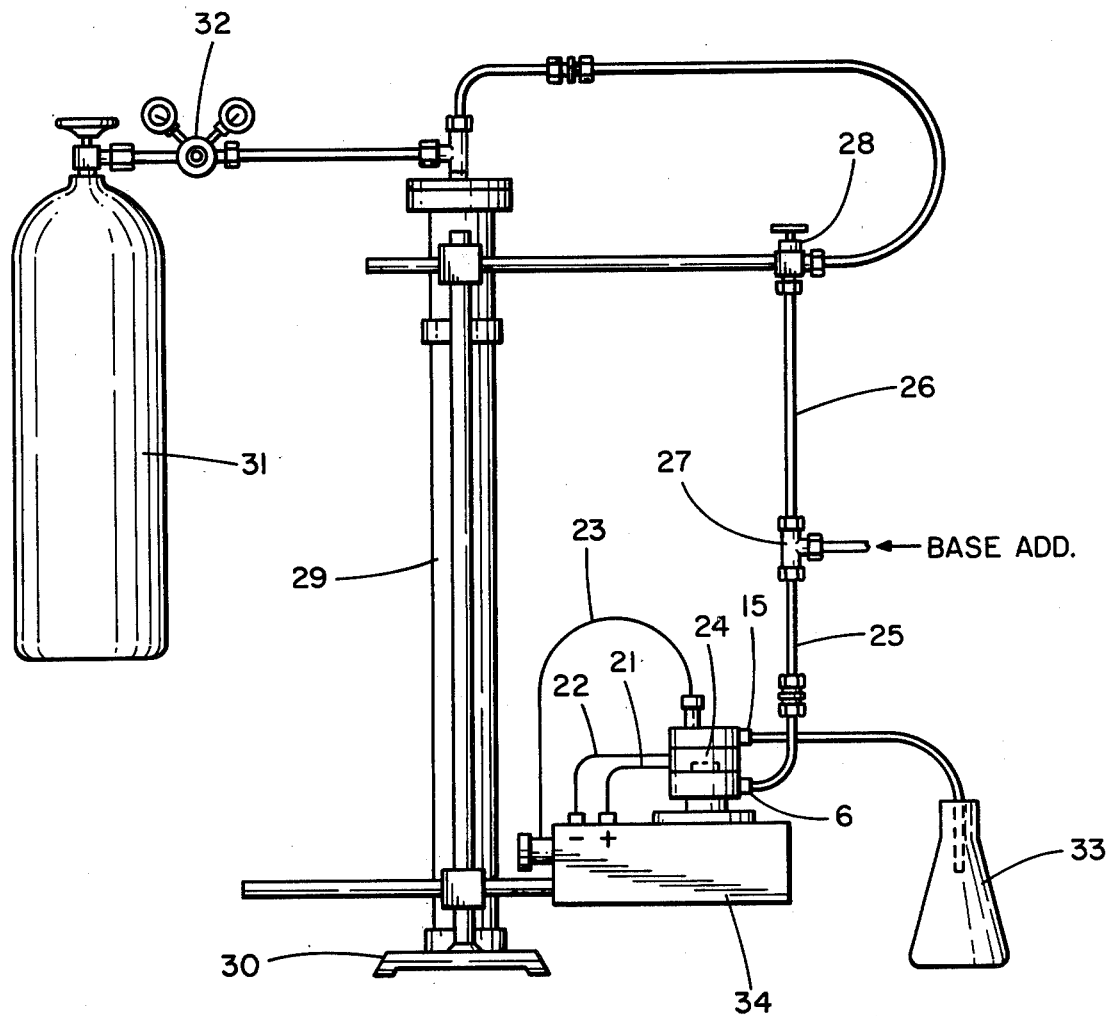
FIG. 3 is a diagramatic sketch of the apparatus of this invention in a test relation.

The assembled electrode 24, shown in FIG. 2, is then joined in the apparatus and the test apparatus, as shown in FIG. 3. The connection 6 communicates through the tubing 6' with the lower end of a mixing column 25, in which the eluting solution containing the separate bands of the organic compounds issuing from the chromatographic separation column 26 is mixed with the alkaline (basic) solution containing the activating ions, introduced by means of a 3-way junction 27.

The solution to be analyzed is introduced into the separation column 26 through the junction 28, as by means of a constant pressure pump 29, support on stand 30. The feed is pressurized inert gas, such as nitrogen from the bottle 31 and the pressure reducing manometer 32.

The upper connection 15 of the electrode is connected to a drain member, such as flask 33. The electrical conductors 21, 22 and 23 are connected to a test apparatus, such as a potentiostat 34.

Thus, the detector is set in the flow stream issuing from the column. The electrode 18 is held at a predetermined positive potential to oxidize the organic components.

EXAMPLE 2

The response and lower detection limit of the amperometric sensor to hydroxy compounds (poly and mono-hydroxy) was determined using a modified version (see note) of the instrument depicted in FIG. 1. The amperometric sensor consisted of a copper oxide/hydroxide working electrode, a platinum counter electrode and a saturated Calomel reference electrode (S.C.E.) in the configuration as shown in FIG. 2. The current measurements were carried out at an applied potential of +450 mV S.C.E. while a solution consisting of 0.10 M LiOH, 1 mM LiCl was pumped through the detector at a flow rate of 0.85 ml/min. 1.8-1800 ng of glucose dissolved in a solution consisting of 0.10 M LiOH and 1 mM LiCl was added to the flowing stream of electrolyte via the injection port. The areas of the observed chromatographic peaks were linear with respect to the amounts of injected glucose. The lower detection limit for glucose at the copper oxide/hydroxide working electrode was found to be in the 100 to 500 picogram range. However, the lower detection limit is strongly affected by the pH of the electrolyte solution. The best results were obtained at pH 13, higher detection limits were observed at pH 14 and pH 12.5.

Similar experimental results were also obtained for glycerol, fructose, galactose and sucrose (non-reducible polysaccharide) as well as for catecholamines such as epinephrine and norepinephrine (aromatic dihydroxy compounds). The lower detection limit for salicylic acid (aromatic monohydrox compound) was found to be in the 1-10 nanogram range.

EXAMPLE 3

The response and lower detection limit of the amperometric sensor to amino compounds was determined using a monified version of the instrument depicted in FIG. 1. The sensor consisted of a nickel oxide/hydroxide working electrode, a platinum counter electrode and a saturated Calomel reference electrode (S.C.E.) in the configuration as shown in FIG. 2. The current measurements were carried out at an applied potential of +450 mV S.C.E. while a solution consisting of 0.10 M LiOH, 1 mM LiCl and 10 $\mu$M NiSO$_4$ was pumped through the detector at a flow rate of 0.85 ml/min. 1.8-1800 nanograms of uric acid dissolved in a solution consisting of 0.10 M LiOH, 1 mM LiCl and 10 $\mu$M NiSO$_4$ were added to the flowing stream of electrolyte via the injection port. The areas of the observed chromatographic peaks were linearly related to the amount of injected uric acid. The lower detection limit for uric acid at the nickel oxide/hydroxide electrode was found to be 100 picograms. However, the lower detection limit of uric acid exhibited similar pH-dependence as that found for glucose in Example 1.

Similar experimental results were obtained for barbiturates such as Phenobarbital and Methoxyhexital. In general, barbiturates as a group exhibit somewhat higher detection limits (0.5-10 nanograms) than uric acid. However, if the barbituate contains a sulphur group such as in thiopental and thiamyl, the sulfur analog exhibit enhanced reactivity at transition metal oxide electrodes and thus shows lower detection limits similar to those of uric acid.

EXAMPLE 4

The response and lower detection limit of the amperometric sensor to thiol compounds was determined using a modified version of the instrument depicted in FIG. 1. The sensor consisted of a silver oxide/hydroxide working electrode, a platinum counter electrode and a S.C.E. reference electrode in a configuration as shown in FIG. 2. The current measurements were carried out at an applied potential of +500 mV while a solution consisting of 0.10 M LiOH was pumped through the detector at a flow rate of 0.85 ml/min. 1.8-1800 nanograms of cysteine dissolved in 0.10 M LiOH was added to the flowing stream of electrolyte via the injection port. The chromatographic peak areas were linearly related to the amount of added cysteine. The lower detection limit for cysteine at the silver oxide/hydroxide electrode was found to be 100 picograms.

EXAMPLE 5

The response and lower detection limit of the amperometric sensor to hydrogen peroxide was determined using the electrodes and conditions as described in Example 1. Linear response was observed for hydrogen peroxide in the 10 nanogram to 1.00 ug range. The lower detection limit for hydrogen peroxide was 10 nanograms.

For thick filmed copper, cobalt, nickel or silver oxide/hydroxide electrodes in alkaline solution and at positive (anodic) applied potentials, the rate determining step in the oxidation process of the organic compounds is the diffusion of charges across the thick oxide/hydroxide layer. The diffusion rate in turn is dependent upon the concentration of cation and anion vacancies within the oxide/hydroxide layer of the electrode.

A high rate of oxidation of organic compounds is believed to be due to a high concentration of cation vacancies. An increase in the cation vacancy concentration and thus an increase in the oxidation rate of organic compounds, can be accomplished by decreasing the anion vacancies concentration, as by doping. The interdependence of cation and anion is given by the Schottky constant $Ks = [Vc+][Va-]$. The observed increase in the oxidation rate at anion doped nickel hydroxide electrode thus is due to the incorporation of anions into the anion vacancies which brings about decrease in the overall anion vacancy concentration. The smaller chloride ion is more effective in decreasing the anion vacancy concentration than the larger bromide or iodide ions. On the other hand, dope ions such as $Li^+$, $Na^+$ or $K^+$ can be incorporated into the cation vacancies and thus decreasing the oxidation rate of organic compounds. The smaller lithium ions are more effective (i.e. much more easily incorporated into the metal oxide/hydroxide matrix) in decreasing the oxidation rate than the larger ions of sodium or potassium.

The improved amperometric sensor device of this invention and its use comprises the steps of providing a metallic substrate selected from the group comprising the multivalent transition metal oxides/hydroxides and, preferably, from the group comprising copper, cobalt, nickel and silver, immersing the metallic substrate in a basic solution of alkali metal hydroxide with a pH within the range of 10 to 14, connecting the metallic substrate to the positive pole of a current source, the negative pole being connected to an auxiliary inactive cathodic electrode (lead, platinum), applying to the metallic substrate a potential of at least 250 mV in respect to a saturated Calomel electrode (S.C.E.) during a time range from 1 to 60 minutes.

Desired results can be secured with a thin oxide coating produced by flash treatment by immersion in an oxidizing solution, but it is preferred to make use of a base electrode on which a thick oxide/hydroxide layer is formed. This can be achieved by carrying out the oxidation reaction to a steady state wherein further oxidation does not result in any appreciable increase in the thickness of the oxide/hydroxide layer.

Moreover, it has been found that the presence of small concentrations of transition metal ions in the basic solution will enhance the long-term performance of the amperometric sensor. For example, the presence of $10^{-5}$ moles/liter $NiSO_4$ contained in a basic solution enables continuous regeneration of the sensor when a nickel oxide/hydroxide is used as amperometric sensor. Concentration within the range of $10^{-3}$ and $10^{-8}$ and preferably $10^{-4} - 10^{-6}$ moles per liter can beneficially be employed.

The advantage of using the above metal oxides/hydroxides electrodes lies in the fact that polyamines and polyhydroxy compounds are catalytically oxidized at these electrodes. The resulting current densities are much larger when compared to current densities observed at inert electrodes (platinum, carbon paste), and at electrodes of the type disclosed in the aforementioned copending application Ser. No. 772,454, in which a platinum or gold electrode is electrolytically plated with conductive lead and nickel oxides.

The amperometric sensor conforming to the present invention exhibits an increased rate of oxidation (10-1000% of aliphatic and aromatic hydroxy compounds (mono- and polyhydroxy) aliphatic and aromatic amides and amines (mono and poly) when doped with alkali metal halides and/or alkaline earth halides. For thick filmed transition metal oxide/hydroxide electrodes, the oxidation rate of the above organic compounds varies with the nature of halide dopants. For example, the rate of glucose oxidation (pH 13, $E_{appl}=30$ 500 mV (S.C.E.)) at a thick filmed nickel hydroxide electrode varies as follows: $Cl^- > BR^- > I^-$. Furthermore, the rate of oxidation also depends upon the nature of the cation employed during the doping process. For example, the rate of glucose oxidation (pH 13, $E_{appl}= +500$ mV (S.C.E.)) at a thick filmed nickel hydroxide electrode was found to vary: $K^+ > Na^+ Li^+$. The improved oxidation rate of the aforementioned compounds at transition metal oxide/hydroxide electrodes depends heavily upon the extent of doping. At very low (0.01%) or very high (4.0%) dopant concentrations the increase in the oxidation rate is 10-25%. At intermediate dopant concentration, the oxidation rate is 25-100% higher than that observed for nondoped electrodes. The optimum oxidation rate is dependent upon the nature and concentration of the dopants (cation as well as anion) and the nature of the transition metal oxide-hydroxide. The application of above improved amperometric sensor for the determination of organic compounds comprises the detection step of separation by conventional chromatographic technique (liquid chromatography or high pressure liquid chromatography).

The eluting solution, containing the separated bands of the organic compounds, is pH 8-16 adjusted with a base such as 1.0 molar (or higher molarity) LiOH, NaOH, or KOH preferably containing $10^{-6}$ to 1.0 molar LiCl, NaCl, KCl or other alkali metal halides. The basidified eluent containing the organic compounds is pumped past an oxide-hydroxide electrode with the above mentioned properties. At a positive (anodic) applied potential, the organic compounds contained in the basidified eluent are oxidized at the metal oxide/hydroxide electrode. The current produced in this oxidation process is directly proportional to the amount of the organic substance present in the eluting chromatography band. The current is recorded as a function of time, thus giving rise to a chromatogram which allows the qualitative as well as quantitative determination of organic compounds.

The transition metal oxide/hydroxide electrodes prepared from copper, cobalt, nickel or silver exhibit catalytic activity in oxidizing mono and polyhydroxy compounds as well as mono and polyamines. In alkaline solutions (pH > 12) and at sufficiently positive (anodic) applied potential, organic hydroxy compounds and amines are readily oxidized. The rate of oxidation is dependent upon the surface concentration of high oxidation state metal oxides and metal hydroxides. These high oxidation state species are known as redox catalysts. Conditions that do not favor the formation of the redox catalyst (low pH solution and/or low applied potential) will also prevent the catalytic oxidation of organic hydroxy compounds and amines. For example, at the nickel oxide/hydroxide electrode, the oxidation of glucose, glycerol, salicylic acid as well as various polyamines in an alkaline solution (0.10 N LiOH) and an applied potential of positive 450 mV (S.C.E.) give rise to a current response of 1-4 $A/cm^2/moles$. However, these current responses are absent if the oxidation is carried out in the same solution but at an applied potential of positive 200 mV (S.C.E.). The optimal applied potential for the catalytic oxidation of hydroxy compounds and amines has been shown to be identical to the electrode potential necessary for the surface formation of high oxidation state redox catalyst.

On the other hand, hydrogen peroxide, uric acid, thiols show high oxidation rates in the presence as well as absence of the redox catalyst. For example, at the nickel oxide/hydroxide electrode the compounds (in 0.10 M LiOH) give rise to high oxidation rates (0.1-4

A/cm$^2$/M) at positive 450 mV (S.C.E.) as well as at positive 250 mV (S.C.E.).

Table 1

| E*$_{appl.}$ (mV vs. SCE) | i$_{(H_2O_2)}$/i$_{(glucose)}$ |
| --- | --- |
| +250 mV | 327.0 |
| +350 mV | 18.0 |
| +450 mV | 0.3 |

*Nickel oxide/hydroxide electrode in 0.10 M LiOH solution. Similar results have been obtained for the copper, cobalt and silver oxide/hydroxide electrodes.

Thus, mono and polyhydroxy compounds and mono and polyamines give large currents at positive 450 mV (SCE, in pH 13 solution) and only insignificant currents at positive 250 mV (SCE). These compounds can be readily distinguished from hydrogen peroxide, thiols, uric acid, and a variety of barbiturates all of which give large currents not only at positive 450 mV but also at positive 250 mV (SCE in pH 13 solution).

Thus, a mixture of electrodeactive compounds is first separated by a HPLC setup. The eluent coming off the chromatographic column is then basidified and pumped through the amperometric sensor. The current produced at transition metal oxide/hydroxide electrode is electronically sampled at positive potential of 450 mV (SCE) and at positive potential of 250 mV (SCE). The currents at the two different applied potentials are monitored simultaneously with a two-channel recorder. The resulting chromatographs which represent recordings of the currents as a function of time indicate large differences for hydroxy compounds and amines at the two applied potentials. This procedure allows the electrochemical differentiation of chromatographic peaks and thus enhances the peak resolution of the chromatograph.

The lower detection limit of the amperometric sensor was determined for a variety of electrode active compounds. The amperometric sensor consisted of a copper working electrode, a platinum counter electrode and a saturated Calomel reference electrode. The measurements were carried out at an applied potential of positive 450 mV (SCE) while a 0.10 M LiOH solution was pumped through the detector at a flow rate of 0.85 ml/min. Under the above conditions, glucose, glycerol, uric acid, salicylic acid, catecholamines, cysteine and a variety of other thiols were detected down to picogram levels ($10^{-9}$ to $10^{-12}$ grams). In all cases, the peak area was found to be directly proportional to the concentration.

The amperometric sensor described in this invention report is superior to presently available spectrophotometric detectors especially with respect to detection limits as well as the variety of clinically important compounds that can be detected.

I claim:

1. A process for preparing an amperometric sensor for use in determining organic polyhydroxy, polyamine, thio and hydrogen peroxide compounds by liquid chromatography and high pressure liquid chromatography comprising immersing a metallic substrate of a transition metal selected of a multivalent transition metal of the periods 4, 5 and 6 of the periodic table, immersing the metallic substrate in an aqueous solution having a pH within the range of 10 to 14 and containing transition metal ions in a concentration within the range of $10^{-3}$ to $10^{-8}$ mole per liter, connecting the metallic substrate as an anode in an electrolytic cell in which the negative pole is connected to an auxiliary inactive electrode, and applying a positive potential of at least 250 mV to the metallic substrate if measured with respect to a saturated Calomel electrode, for a time sufficient to form a high valence oxide-hydroxide coating on the substrate by anodic oxidation and then rinsing the sensor device with water.

2. A process as claimed in claim 1 in which the metallic substrate is immersed in an aqueous solution of an alkali metal hydroxide.

3. A process as claimed in claim 1 in which the potential is applied for a period of time ranging from 1 to 60 minutes.

4. A process as claimed in claim 1 in which the aqueous solution contains bivalent nickel cations in a concentration within the range of $10^{-4}$ to $10^{-6}$ moles per liter.

5. A process as claimed in claim 1 in which the concentration of transition metal ions in the aqueous solution is within the range of $10^{-4}$ to $10^{-6}$ mole per liter.

6. A process as claimed in claim 1 in which the transition metal ions in the aqueous solution are ions of the transition metal of the substrate.

7. The method as claimed in claim 1 in which the transition metal is selected from the group consisting of copper, cobalt, nickel and silver.

* * * * *

UNITED STATES PATENT OFFICE
CERTIFICATE OF CORRECTION

Patent No. 4,183,791    Dated January 15, 1980

Inventor(s) Karl G. Schick

It is certified that error appears in the above-identified patent and that said Letters Patent are hereby corrected as shown below:

Col. 5, line 65, cancel "30" and substitute -- $\pm$ --

Signed and Sealed this

Tenth Day of June 1980

[SEAL]

Attest:

SIDNEY A. DIAMOND

Attesting Officer    Commissioner of Patents and Trademarks